US 6,551,804 B2

(12) United States Patent
DiCosimo et al.

(10) Patent No.: US 6,551,804 B2
(45) Date of Patent: Apr. 22, 2003

(54) PROCESS FOR PREPARING 4-CYANOPENTANOIC ACID

(75) Inventors: Robert DiCosimo, Rockland, DE (US); Robert D. Fallon, Elkton, MD (US); John E. Gavagan, Wilmington, DE (US)

(73) Assignee: E. I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/766,955

(22) Filed: Jan. 22, 2001

(65) Prior Publication Data

US 2002/0164728 A1 Nov. 7, 2002

Related U.S. Application Data

(63) Continuation-in-part of application No. 09/352,015, filed on Jul. 12, 1999, now Pat. No. 6,251,646.

(51) Int. Cl.[7] .................................................. C12P 13/00
(52) U.S. Cl. ....................................... 435/128; 435/136
(58) Field of Search ................................. 435/128, 136

(56) References Cited

U.S. PATENT DOCUMENTS

| | | | |
|---|---|---|---|
| 4,288,552 A | | 9/1981 | Gestrelius |
| 4,343,900 A | * | 8/1982 | Watanabe |
| 4,355,105 A | | 10/1982 | Lantero, Jr. |
| 5,705,382 A | * | 1/1998 | Endo et al. |
| 5,814,508 A | | 9/1998 | DiCosimo et al. |
| 5,858,736 A | | 1/1999 | DiCosimo et al. |
| 5,908,954 A | | 6/1999 | DiCosimo et al. |
| 5,922,589 A | | 7/1999 | DiCosimo et al. |
| 5,936,114 A | | 8/1999 | DiCosimo et al. |
| 5,998,180 A | | 12/1999 | Armitage et al. |
| 6,066,490 A | | 5/2000 | DiCosimo et al. |
| 6,077,955 A | | 6/2000 | DiCosimo et al. |

FOREIGN PATENT DOCUMENTS

| | | |
|---|---|---|
| CA | 2103616 | 2/1994 |
| WO | WO-2001004278 A1 * | 1/2001 |

OTHER PUBLICATIONS

Cooling et al. Chemoenzymatic production of 1,5–dimethyl–2–piperidone (Jan. 22, 2001) Journal of Molecular Catalysis B–Enzymatic, vol. 11, No. 4–6, pp. 295–306.*
Kobayashi et al. Tetrahedron 46:5587–5590 (1990).
Kobayashi et al. J. Bacteriology 172, 4807–4815 (1990).
Almatawah et al., Extremophiles 3: 283–291 (1999).
S. Levy–Schil et al., Gene 161:15–20 (1995).
Gavagan et al., J. Org. Chem., 63:4792–4801 (1998).
Cowan et al., Extremophiles 2:207–216 (1998).
Bucke, Methods in Enzymology 135: 175–189 (1987).
Chibata et al., Methods in Enzymology 135:189–198 (1987).
Chibata, In Immobilized Microbial Cells; Venkatsubramanian K., Ed.:ACS Symposium Series 106; American Chemical Society; Washington, DC, 1979, pp 187–201.
Birnbaum et al., Biotechnol. Lett. 3:394–400 (1981).

* cited by examiner

*Primary Examiner*—Irene Marx

(57) ABSTRACT

This invention relates to an improved process for preparing a carboxylic acid from the corresponding nitrile using a nitrilase catalyst. More particularly, the instant invention converts 2-methylglutaronitrile to 4-cyanopentanoic acid in aqueous solution using an enzyme catalyst having an nitrilase activity, immobilized in alginate, and crosslinked with glutaraldehyde and polyethylenimine.

8 Claims, No Drawings

PROCESS FOR PREPARING 4-CYANOPENTANOIC ACID

This application is a continuation-in-part of U.S. application Ser. No. 09/352,015, filed Jul. 12, 1999, which subsequently issued as U.S. Pat. No. 6,251,646, on Jun. 26, 2001.

FIELD OF THE INVENTION

This invention relates to an improved process for converting a nitrile to the corresponding carboxylic acid by using an enzyme catalyst having nitrilase activity. More particularly, the instant invention converts 2-methylglutaronitrile to the ammonium salt of 4-cyanopentanoic acid in aqueous solution using an enzyme catalyst having an aliphatic nitrilase (EC 3.5.5.7) activity.

BACKGROUND OF THE INVENTION

A nitrilase enzyme directly converts a nitrile to the corresponding carboxylic acid ammonium salt in aqueous solution without the intermediate formation of an amide. Nitrilases have been identified in a variety of microorganisms, for example, Kobayashi et al. (*Tetrahedron* 46:5587–5590 (1990); *J. Bacteriology*, 172:4807–4815 (1990)) have described an aliphatic nitrilase isolated from *Rhodococcus rhodochrous* K22 that catalyzed the hydrolysis of aliphatic nitrites to their corresponding carboxylic acid ammonium salts. A stereospecific nitrilase of *Alcaligenes faecalis* 1650 has been used to resolve racemic nitrites in the manufacture of chiral carboxylic acids, and the gene encoding the nitrilase has been cloned and expressed (WO 00/23577). A nitrilase has been isolated from the thermophilic bacterium *Bacillus pallidus* strain Dac521 that catalyzed the hydrolysis of aliphatic, aromatic and heterocyclic nitrites (Almatawah et al., *Extremophiles* 3:283–291 (1999)). A nitrilase from *Rhodococcus rhodochrous* NCIMB 40757 or NCIMB 40833 has been used to convert acrylonitrile to ammonium acrylate (U.S. Pat. No. 5,998,180). A nitrilase from *Comamonas testosteroni* has been isolated that can convert a range of aliphatic α,ω-dinitriles to either the corresponding ω-cyanocarboxylic acid ammonium salt or dicarboxylic acid diammonium salt (CA 2,103,616; S. Lévy-Schil et al., *Gene* 161:15–20 (1995)). The regioselective hydrolysis of aliphatic α,ω-dinitriles to the corresponding ω-cyanocarboxylic acid ammonium salts by the nitrilase activity of *Acidovorax facilis* 72W has also been reported (Gavagan et al., *J. Org. Chem.*, 63:4792–4801 (1998)).

A combination of two enzymes, nitrile hydratase and amidase, can also be used to convert aliphatic nitrites to the corresponding carboxylic acid ammonium salts in aqueous solution. Here the aliphatic nitrile is initially converted to an amide by the nitrile hydratase and then the amide is subsequently converted by the amidase to the corresponding carboxylic acid ammonium salt. A wide variety of bacterial genera are known to possess a diverse spectrum of nitrile hydratase and amidase activities, including Rhodococcus, Pseudomonas, Alcaligenes, Arthrobacter, Bacillus, Bacteridium, Brevibacterium, Corynebacterium, and Micrococcus. Cowan et al. (*Extremophiles* 2:207–216 (1998)) have recently reviewed both the nitrilase and nitrile hydratase/amidase enzyme systems of nitrile-degrading microorganism.

2-Methylglutaronitrile is one example of an aliphatic α,ω-dinitrile that can be regioselectively converted to a ω-cyanocarboxylic acid ammonium salt (i.e., the ammonium salt of 4-cyanopentanoic acid) using a biocatalyst. The biocatalytic preparation of 4-cyanopentanoic acid has been described previously in U.S. Pat. No. 5,814,508 and its divisionals U.S. Pat. Nos. 5,858,736, 5,908,954, 5,922,589, 5,936,114, 6,077,955, and U.S. Pat. No. 6,066,490. These patents relate to a process in which an aliphatic α,ω-dinitrile is converted to an ammonium salt of an ω-cyanocarboxylic acid in aqueous solution using a catalyst having an aliphatic nitrilase (EC 3.5.5.7) activity, or a combination of nitrile hydratase (EC 4.2.1.84) and amidase (EC 3.5.1.4) activities. When the aliphatic α,ω-dinitrile is also unsymmetrically substituted at the ω-carbon atom, the nitrilase produces the ω-cyanocarboxylic acid ammonium salt resulting from hydrolysis of the ω-nitrile group with greater than 98% regioselectivity. U.S. Pat. No. 5,814,508 specifically discloses a method for converting 2-methylglutaronitrile to 4-cyanopentanoic acid in aqueous solution, where *Acidovorax facilis* 72W is subjected to a 10–120 minute heat treatment (35–70° C.) before use as an enzyme catalyst. This heat treatment was critical to select for the desirable regioselective aliphatic nitrilase (EC 3.5.5.7) activity while destroying an undesirable, non-regioselective nitrile hydratase activity. 4-Cyanopentanoic acid can then serve as substrate in a one-step chemical process for the commercial preparation of 1,5-dimethyl-2-piperidone. 1,5-Dimethyl-2-piperidone has many uses as an industrial solvent, including electronics cleaning, photoresist stripping, industrial degreasing and metal cleaning, resin cleanup, ink formulations, industrial adhesives, and as a reaction solvent for polymers and chemicals.

For commercial-scale applications using a biocatalyst, immobilizing microbial cells has many known economical advantages compared to the use of unimmobilized cells. Some advantages are the capacity to use them repeatedly, their ease of separation, and their use in continuous reactions. Cell inclusion into a polymer matrix permits entrapment of living or metabolically inactive cells while maintaining high diffusion of product and substrate. Examples of typical matrices for immobilization are sodium alginate (Bucke, *Methods in Enzymology* 135:175–189 (1987)) or carrageenan (Chibata et al., *Methods in Enzymology* 135:189–198 (1987)). Methods of entrapment are relatively simple, and gel material is non-toxic and low priced.

"Operational" stability of immobilized cells can be further increased by subsequent treatment of the cell beads with crosslinking agents that covalently crosslink cells with multifunctional reagents, such as glutaraldehyde and polyethylenimine or hexamethylenediamine. In one example, stability was studied with respect to immobilized *E. coli* cells in kappa-carrageenan for the production of L-aspartic acid (Chibata, I. In *Immobilized Microbial Cells*; Venkatsubramanian, K., Ed.; ACS Symposium Series 106; American Chemical Society; Washington, D.C., 1979, pp 187–201). With optimized concentrations of hexamethylenediamine and glutaraldehyde used as a crosslinking treatment, the half-life of immobilized cells was remarkably extended to over five times that of untreated immobilized cells.

Furthermore, Birnbaum et al. (*Biotechnol. Lett.* 3:393–400 (1981)) disclose methods of increasing the physical stability of calcium alginate immobilized cells. One stabilization method uses polyethylenimine treatment (24 hours), followed by glutaraldehyde cross-linking (1–5 minutes). Bead stability was examined by incubating the immobilized cells in 0.1 M sodium phosphate buffer for ten days. Little cell release was noted from the immobilized cells, thereby demonstrating improved bead integrity. At the same time, overall catalyst activity was detrimentally affected by this protocol. Birnbaum suggests this effect was likely due to glutaraldehyde toxicity.

Finally, the preferred order of adding polyethylenimine and glutaraldehyde for directly immobilizing whole microbial cells or microbial cell material has been understood to depend on the sensitivity of the immobilized enzyme activity to glutaraldehyde. U.S. Pat. No. 4,288,552 discloses that glutaraldehyde-sensitive enzymes (such as thiol-enzymes and others with an SH group in or very near the active site of the enzyme molecule) are inactivated by thiol-reactive agents such as glutaraldehyde. For these types of enzyme catalysts, the invention requires that the microbial cell material be treated with polyethylenimine first, the glutaraldehyde being added simultaneously or subsequently, to negate potential loss of enzyme activity. In contrast, U.S. Pat. No. 4,355,105 teaches that it is desirable to introduce glutaraldehyde before polyethylenimine when immobilizing microorganisms whose enzymes are not sensitive to glutaraldehyde. In this instance the resulting immobilized cells are more readily recovered from the aqueous medium than cells immobilized with polyethylenimine pretreatment before glutaraldehyde addition. In neither case are microbial cells entrapped in a gel or polymer matrix before treatment with polyethylenimine and glutaraldehyde.

The problem to solved, therefore, is developing an economical method for producing immobilized cell catalyst having high specific activity and a prolonged period of physical integrity when used as catalyst for converting a nitrile to the corresponding carboxylic acid ammonium salt. More specifically, the art would be advanced by a process using an enzyme catalyst that results in higher yields and higher concentrations of 4-cyanopentanoic acid, and is also more convenient to use than those previously disclosed.

SUMMARY OF THE INVENTION

Applicants' invention is a method for producing a carboxylic acid comprising: a) immobilizing in alginate an enzyme catalyst characterized by a nitrilase activity; b) adding, to the immobilized enzyme catalyst of step a), a first stabilizer and then a second stabilizer, each in an amount and for a time sufficient to crosslink the immmobilized enzyme catalyst, the first stabilizer and the second stabilizer each selected from the group consisting of glutaraldehyde and polyethylenimine, provided the second stabilizer is other than the first stabilizer; c) contacting the product of step b) with a nitrile in a suitable aqueous reaction mixture; d) isolating the carboxylic acid produced in step c) in the form of a salt or an acid; and e) optionally repeating steps c) and d) at least one time. Preferred embodiments of the invention include where the nitrile of step c) is 2-methylglutaronitrile; the aqueous reaction mixture of step c) has a $NH_4^+:Ca^{2+}$ ratio greater than 20:1 (more preferably greater than 200:1, and most preferably greater than 750:1) during the course of the reaction; and the carboxylic acid isolated in step d) is 4-cyanopentanoic acid.

The preferred enzyme catalysts are *Acidovorax facilis* 72W (ATCC 55746), *Acidovorax facilis* 72-PF-15 (ATCC 55747), *Acidovorax facilis* 72-PF-17 (ATCC 55745), *Escherichia coli* SS1001 (ATCC PTA-1177), or *Escherichia coli* SW9 (ATCC PTA-1175), and the enzyme catalyst are in the form of whole cells or permeabilized microbial cells. When the enzyme catalyst is *Acidovorax facilis* 72W (ATCC 55746) there is no need to inactivate the nitrile hydratase activity of the enzyme catalyst by a heat treatment before its immobilization in alginate.

BRIEF DESCRIPTION OF THE BIOLOGICAL DEPOSITS

Applicants have made the following biological deposits under the terms of the Budapest Treaty:

| Depositor Identification Reference | Int'l. Depository Designation | Date of Deposit |
|---|---|---|
| *Acidovorax facilis* 72-PF-17 | ATCC 55745 | 8 Mar. 1996 |
| *Acidovorax facilis* 72W | ATCC 55746 | 8 Mar. 1996 |
| *Acidovorax facilis* 72-PF-15 | ATCC 55747 | 8 Mar. 1996 |
| *Escherichia coli* SS1001 | ATCC PTA-1177 | 11 Jan. 2000 |
| *Escherichia coli* SW91 | ATCC PTA-1175 | 11 Jan. 2000 |

As used herein, "ATCC" refers to the American Type Culture Collection International Depository located 10801 University Blvd., Manassas, Va. 20110-1109, U.S.A. The "ATCC No." is the accession number to cultures on deposit with the ATCC. The listed deposits will be maintained in the indicated international depository for at least thirty (30) years and will be made available to the public upon grant of a patent disclosing it. The availability of a deposit does not constitute a license to practice the subject invention in derogation of patent rights granted by government action.

DETAILED DESCRIPTION OF THE INVENTION

The instant invention relates to an improved process for converting a nitrile to the corresponding carboxylic acid ammonium salt using an enzyme catalyst having nitrilase activity. More particularly, the instant invention converts 2-methylglutaronitrile to the ammonium salt of 4-cyanopentanoic acid in aqueous solution using an enzyme catalyst having an aliphatic nitrilase (EC 3.5.5.7) activity. Applicants now disclose that it is possible to immobilize an enzyme catalyst having nitrilase activity in calcium alginate, and, after crosslinking with glutaraldehyde and polyethylenimine, use the resulting catalyst to produce 4-cyanopentanoic acid ammonium salt at concentrations of at least 1.50 M under conditions which were expected to result in the rapid loss of physical integrity of the crosslinked immobilized enzyme catalyst. It was unexpected that a glutaraldehyde treatment of the immobilized cells prior to the addition of PEI could be performed without any measurable loss of nitrilase activity, or that operating the reaction at a ratio of ammonium/calcium ion of at least 750:1 would not affect the physical integrity of the catalyst beads when it has been recommended not to exceed a ratio of 20:1. The enzyme catalyst was reused in many consecutive recycle reactions with no loss of physical integrity.

Applicants additionally disclose that (in contrast to the corresponding enzyme catalyst prepared using carrageenan) the nitrilase activity of glutaraldehyde/polyethylenimine-crosslinked alginate-immobilized enzyme catalyst increases with increasing concentration of dry cell weight in the catalyst beads. The use of the alginate-immobilized enzyme catalyst is advantageous in that it increases the overall product yield based on catalyst usage when compared to a carrageenan-immobilized enzyme catalyst.

Applicants additionally disclose that in the case of immobilizing the enzyme catalyst *Acidovorax facilis* 72W, the heat-treatment normally required to inactivate an undesirable nitrile hydratase activity was not required when the cells were immobilized in alginate and the resulting enzyme catalyst crosslinked with the stabilizers glutaraldehyde and polyethylenimine. It was unexpected that the immobilization procedure would selectively and completely inactivate the undesirable nitrile hydratase activity, without producing a measurable loss of nitrilase activity, particularly when it is known that the nitrilase can be inactivated by glutaraldehyde.

The process improvements disclosed herein, when compared to previously known methods, result in higher yields of the product (based on weight of product per weight of catalyst) at higher concentrations than previously obtained. The product of the claimed process is useful as a precursor for polymers, solvents (e.g., 1,5-dimethyl-2-piperidone), and chemicals of high value in the agricultural and pharmaceutical industries.

In the application, unless specifically stated otherwise, the following abbreviations and definitions apply:

"Glutaraldehyde" is abbreviated GA.

"Polyethylenimine" is abbreviated PEI.

"2-Methylglutaronitrile" is abbreviated 2-MGN.

"4-Cyanopentanoic acid" is abbreviated 4-CPA.

"Enzyme catalyst" refers to a catalyst that is characterized by a nitrilase activity. The catalyst may be in the form of a whole microbial cell or permeabilized microbial cell(s).

"Aqueous reaction mixture" is used to refer to an aqueous mixture containing water, a calcium salt at a concentration of at least 2 mM, and optionally, a buffer capable of maintaining the initial pH of the reaction between 5 and 10, preferably between 6 and 8.

"Aqueous product mixture" is used to refer to an aqueous mixture containing a product resulting from the corresponding process step.

Significant improvements to the process for conversion of 2-methylglutaronitrile (2-MGN) to 4-cyanopentanoic acid (4-CPA) ammonium salt are now disclosed. Specifically, the significant improvements of the instant invention result from a process having the following steps: 1) immobilizing an enzyme catalyst characterized by a nitrilase activity, preferably derived from *Acidovorax facilis* 72W, in alginate, 2) sequentially adding glutaraldehyde and polyethylenimine (preferably in that order) to the immobilized enzyme catalyst in suitable amounts and for times sufficient to effect each stabilizers' crosslinking, 3) contacting 2-MGN with the crosslinked immobilized enzyme catalyst in a suitable aqueous reaction mixture, 4) isolating 4-CPA as the acid or an ammonium salt, and 5) then recycling the crosslinked immobilized enzyme catalyst at least one time. The advantages of the instant invention can also be realized when using other enzyme catalysts characterized by nitrilase activity (for example, *Rhodococcus rhodochrous, Alcaligenes faecalis, Bacillus pallidus, Comamonas testosteroni,* Nocardia sp., Acinetobacter sp., and Arthrobacter sp.), for converting a nitrile to the corresponding carboxylic acid ammonium salt.

Enzyme Catalyst Immobilization

Methods for immobilizing the enzyme catalyst were developed using two different polymer matrices, sodium alginate and kappa-carrageenan. Enzyme catalysts in the form of whole cells or permeabilized microbial cells can be immobilized in alginate or carrageenan; methods for permeabilization are well-known to those skilled in the art, and include, but are not limited to, freeze-thaw, or treatment with organic solvents or detergents (Felix, *Bioprocess. Technol.* 11:259–278 (1991); Felix, *Anal. Biochem.* 120:211–234 (1982)). Cell immobilization in alginate is advantageous, since the immobilization can be done at temperatures as low as 5° C. In contrast, carrageenan immobilization typically requires temperatures of 45–50° C., which can result in inactivation of the nitrilase.

Glutaraldehyde (GA) and polyethylenimine (PEI) treatments were added to the immobilization protocols to further increase the mechnical stability of the beads, such that they would be amenable to a high number of consecutive reactions with catalyst recycle. The amount of GA and PEI added to crosslink the alginate bead enzyme catalysts each ranged from 25 wt % per dry cell weight present in the catalyst beads, to 2 wt % per dry cell weight present in the catalyst beads, where the ratio of GA to PEI added to the catalyst beads also ranged from 3:1 to 1:3. The two crosslinking stabilizers are added to the immobilized enzyme catalysts in either order: GA first, then PEI, or PEI first, then GA. The preferred order of adding the two-crosslinking stabilizers was GA first, followed by PEI. The addition of the second stabilizer is delayed for a time sufficient to permit crosslinking by the first stabilizer. The time for GA-crosslinking of the immobilized enzyme catalysts ranged from 5 min to 2 h, preferably 30 min to 1 h. The time for PEI crosslinking of the immobilized enzyme catalysts ranged from 30 min to 24 h, preferably 1 h to 12 h.

It was unknown and unexpected that a combination of GA/PEI would successfully stabilize the immobilized cell catalysts without damage to the specific nitrilase activity, since it was known that glutaraldehyde inactivates the *Acidovorax facilis* 72W nitrilase enzyme (Example 1). In Cowan et al., (*Extremophiles* 2:207–216 (1998)) it is disclosed that nitrilase enzymes function by the nucleophilic attack on the nitrile carbon by an activated thiol residue; U.S. Pat. No. 4,288,552 notes that glutaraldehyde-sensitive enzymes, such as thiol-enzymes, are inactivated by glutaraldehyde.

It has been reported that calcium-crosslinked alginate is not stable in the presence of high concentrations of other cations. Specifically, it is not recommended to exceed a ratio of ammonium/calcium ion of 20:1 or 25:1 (Klein, J. and Vorlop, K. D., In *Biotechnology Focus I;* Finn, R. F., Ed.; Oxford University Press: New York; 1998, pp 325–336; Smidsrod et al., *Trends Biotechnol.* 8, 71–78 (1990)). Klein et al. states that the ratio of electrolytes (molar sum of $Na^+$, $K^+$, $NH_4^+$, $Mg^{2+}$) to $Ca^{2+}$ should not be higher than 20:1 for alginates with a high proportion of L-guluronic acid. In the instant application, after crosslinking with glutaraldehyde and polyethylenimine, the alginate gel enzyme catalysts (which contain a high proportion of L-guluronic acid), retain their physical integrity when recycled in at least 195 consecutive batch reactions to produce high concentrations of 4-cyanopentanoic acid ammonium salt. In these reactions, which contain a minimum calcium ion concentration of 2 mM, the ratio of ammonium ion to calcium ion is typically at least 750:1 (see Example 4). Reactions have been run where the ratio of ammonium ion to calcium ion was 200:1, 750:1, and 950:1. These results certainly could not have been predicted.

When running commercial processes, it is desirable to have high specific activities, here defined as enzyme activity/weight of catalyst. In the instant application, nitrilase-specific activity increased with increasing concentration of dry cell weight in alginate beads, but not in carrageenan beads. With carrageenan beads, there was either a small increase of activity (7%) with a 50% increase in dry cell weight at 30° C., or a slight decrease in specific activity at 35° C. (see Example 4).

Immobilization of *Acidovorax facilis* 72W (ATCC 55746) in Glutaraldehyde/Polyethylenimine-crosslinked Alginate The microbe *Acidovorax facilis* 72W (ATCC 55746) has been previously isolated from soil samples exposed to aliphatic nitriles or dinitriles (U.S. Pat. No. 5,814,508 and its divisionals U.S. Pat. Nos. 5,858,736, 5,908,954, 5,922,589, 5,936,114, 6,077,955, and U.S. Pat. No. 6,066,490). (U.S. Pat. No. 5,814,508 is hereby incorporated by reference.) When *Acidovorax facilis* 72W is used as a microbial whole-cell catalyst for the hydrolysis of unsymmetrically substituted α-alkyl-α,ω-dinitriles, the corresponding dicarboxylic acid monoamides and dicarboxylic acids are produced in addition to the desired ω-cyanocarboxylic acid. An undesirable non-regioselective nitrile hydratase activity of this whole-cell catalyst produced the undesirable dicarboxylic acid monoamides, which were further converted by an amidase to the corresponding dicarboxylic acid. Enzyme catalysts such as *Acidovorax facilis* 72-PF-15, *Acidovorax facilis* 72-PF-17, *Escherichia coli* SS1001 and *Escherichia coli* SW91, which are characterized by the nitrilase activity of *Acidovorax facilis* 72W but do not exhibit the nitrile hydratase activity of *Acidovorax facilis* 72W, do not produce the undesirable dicarboxylic acid monoamide and dicarboxylic acid byproducts.

Heating a suspension of *Acidovorax facilis* 72W (ATCC 55746) in a suitable buffer at 35–70° C. for a short period of time was found to deactivate the undesirable nitrile hydratase activity without affecting the desirable nitrilase activity. Thus, previous processes for hydrolysis of 2-methylglutaronitrile (2-MGN) to 4-cyanopentanoic acid (4-CPA) ammonium salt with extremely high regioselectivity required that suspensions of *Acidovorax facilis* 72W be heat-treated at 35–70° C. to inactivate unwanted nitrile hydratase activity and eliminate the production of the unwanted byproduct 2-methylglutaric acid (Gavagan et al., *Appl. Microbiol. Biotechnol.*, 52:654–659 (1999); U.S. Pat. No. 5,814,508). This heat-treatment did not produce any loss of nitrilase activity, and was also routinely used in preparing immobilized cell catalysts.

This invention for the commercial production of 4-cyanopentanoic acid provides the further benefit that immobilizing of non-heat-treated *Acidovorax facilis* 72W cells in alginate removes approximately 90% of unwanted nitrile hydratase activity. Subsequent glutaraldehyde (GA) or glutaraldehyde and polyethylenimine (GA/PEI) crosslinking of alginate-immobilized *Acidovorax facilis* 72W cells further reduces the rate of production of undesirable byproducts (2-methylglutaric acid) by the catalyst to that observed with cells that were heat-treated and had no detectable nitrile hydratase activity (see Example 10). Applicants' disclosure is surprising and unexpected, since the heat treatment step heretofore required in U.S. Pat. No. 5,814,508 is no longer needed. It was unknown that the immobilization of *Acidovorax facilis* 72W cells in alginate, followed by GA or GA/PEI-crosslinking, would selectively and completely inactivate an undesirable nitrile hydratase activity, while at the same time causing no measurable loss in the desirable nitrilase activity. This result is particularly unexpected as it was known that nitrilase is inactivated by glutaraldehyde.

Hydrolysis of 2-Methylglutaronitrile

The temperature of the hydrolysis reaction is chosen to optimize both the reaction rate and the stability of the enzyme catalyst activity. The temperature of the reaction may range from just above the freezing point of the suspension (ca. 0° C.) to 60° C., with a preferred range of reaction temperature of from 5° C. to 35° C. The immobilized enzyme catalyst suspension may be prepared by suspending the catalyst in distilled water, or in a aqueous solution of a buffer which will maintain the initial pH of the reaction between 5.0 and 10.0, preferably between 6.0 and 8.0. As the reaction proceeds, the pH of the reaction mixture may change due to the formation of an ammonium salt of the carboxylic acid from the corresponding nitrile functionality of the dinitrile. The reaction can be run to complete conversion of dinitrile with no pH control, or a suitable acid or base can be added over the course of the reaction to maintain the desired pH. A calcium salt, including but not limited to calcium chloride or calcium acetate, is added to the hydrolysis reaction at a concentration of at least 2 mM to maintain the physical integrity of the crosslinked immobilized enzyme catalyst.

4-Cyanopentanoic acid may also be isolated from the product mixture (after removal of the catalyst) by adjusting the pH of the reaction mixture to between 2.0 and 2.5 with concentrated HCl, saturating the resulting solution with sodium chloride, and extracting 4-cyanopentanoic acid with a suitable organic solvent (such as ethyl acetate, ethyl ether, or dichloromethane). The organic extracts are then combined, stirred with a suitable drying agent (e.g., magnesium sulfate), filtered, and the solvent removed (e.g., by rotary evaporation) to produce the desired product in high yield and in high purity (typically 98–99% pure). If desired, the product can be further purified by recrystallization or distillation. Alternatively, the 4-cyanopentanoic acid ammonium salt may be used directly in a subsequent reaction, as is the case in the preparation of 1,5-dimethyl-2-piperidone (U.S. Pat. No. 5,814,508 and its divisionals U.S. Pat. Nos. 5,858,736, 5,908,954, 5,922,589, 5,936,114, 6,077,955 and U.S. Pat. No. 6,066,490).

EXAMPLES

In the following examples, which serve to further illustrate the invention and not to limit it, the % recovery of 2-methylglutaronitrile and the % yields of the hydrolysis products 4-cyanopentanoic acid and 2-methylglutaric acid formed during the microbial hydrolysis reactions were based on the initial amount of 2-methylglutaronitrile present in the reaction mixture (unless otherwise noted), and determined by HPLC using a refractive index detector and a Supelcosil LC-18-DB column (15 cm×4.6 mm dia.), and an eluent composed of 10 mM acetic acid, 10 mM sodium acetate, and 7.5% (v/v) methanol in water.

The meaning of abbreviations is as follows: "sec" means second(s), "min" means minute(s), "h" means hour(s), "d" means day(s), "μ" means microliter, "mL" means milliliters, "L" means liters, "mm" means millimeters, "nm" means nanometers, "mM" means millimolar, "M" means molar, "mmol" means millimole(s), "μmole" mean micromole", "g" means gram, "μg" means microgram, "ng" means nanogram, "U" means units, and "dcw" means dry cell weight.

Example 1

Inactivation of *Acidovorax facilis* 72W Nitrilase Enzyme by Glutaraldehyde

Example 1 illustrates that glutaraldehyde is toxic to nitrilase activity.

The nitrilase of *Acidovorax facilis* 72W (ATCC 55746) was isolated from a cell extract and refined to >90% purity by passage through a Q-Sepharose ion exchange medium followed by gel filtration on a Hiload 16/60 Superdex 200 column. Nitrilase activity was monitored during purification by measuring the rate of conversion of benzonitrile to benzoic acid as indicated by the increase in absorption at 245 nm of a 5 mM solution of benzonitrile in 100 mM phosphate buffer (pH 7.2). The nitrilase activity of the purified enzyme was 25.7 U/mg protein. When the enzyme assay was performed in the presence of glutaraldehyde (0.10 M), the nitrilase-specific activity decreased to 6.65 U/mg, a 74% loss of enzyme activity.

Example 2

Immobilization of *Acidovorax facilis* 72W Cells in Calcium Alginate

Example 2 illustrates the immobilization of *Acidovorax facilis* 72W (ATCC 55746) cells in both uncrosslinked and GA/PEI-crosslinked calcium alginate.

Into a 100-mL media bottle equipped with magnetic stir bar and containing 22.9 g of distilled, deionized water at 50° C. was slowly added 1.10 g of FMC BioPolymer Protanal® LF 10/60 alginate with rapid stirring. The mixture was heated to 75–80° C with rapid stirring until the alginate was completely dissolved, and the resulting solution cooled to 25° C. in a water bath. A suspension of *Acidovorax facilis* 72W (50% wet cell weight, 11.5% dry cell weight) in 0.15 M sodium acetate buffer (16 mL total volume, pH 7.0) was heated to 50° C. for 15 min, then cooled to 25° C. and added to the alginate solution at 25° C. with stirring. The cell/alginate mixture was added dropwise by syringe to 213 mL of 0.20 M calcium acetate buffer (pH 7.0) at 25° C. with stirring. After stirring for 2 h, the buffer was decanted from the resulting beads, which were resuspended in 84 mL of 0.20 M calcium acetate buffer (pH 7.0) at 25° C. With stirring, 0.88 g of 25 wt % glutaraldehyde (GA) in water was added and the beads mixed for 1.0 h at 25° C. To the suspension was then added 3.5 g of 12.5 wt % polyethylenimine (PEI) (BASF Lupasol® PR971L, average molecular weight ca. 750,000) in water, and the beads mixed for an additional 1 h at 25° C. The crosslinked beads were then washed twice with 84 mL of 0.20 M calcium acetate buffer (pH 7.0) at 25° C, and stored in this same buffer at 5° C.

Uncrosslinked beads were prepared by the above-described process except that GA and PEI were not added to the suspension of beads in 0.20 M calcium acetate buffer.

Example 3

Comparison of Uncrosslinked and GA/PEI-crosslinked *Acidovorax facilis* 72W Cell/Alginate Bead Catalyst for Production of 4-Cyanopentanoic Acid Example 3 illustrates that GA/PEI-crosslinked catalyst beads produced higher yields of 4-cyanopentanoic acid in consecutive batch reactions than uncrosslinked beads.

Into separate 125-mL jacketed reaction vessels (temperature-controlled at 30° C. with a recirculating temperature bath) was placed 16.5 g of either uncrosslinked or GA/PEI-crosslinked *Acidovorax facilis* 72W cell/alginate beads prepared as described in Example 2. To each reaction vessel was added 68.25 mL of distilled, deionized water, 1.0 mL of 0.50 M calcium acetate buffer (pH 7.0, 5.0 mM final calcium ion concentration in reaction mixture) and 14.25 mL (13.54 g, 1.25 M) of 2-methyglutaronitrile, and the mixture stirred at 30° C. Samples (0.100 mL) of the reaction mixture were mixed with 0.400 mL of water, and then 0.360 mL of the diluted sample was mixed with 0.040 mL of 0.75 M N-methylpropionamide (HPLC external standard) in water and 0.020 mL of 6.0 N HCl. The resulting mixture in each vessel was filtered (0.22 µm) and the filtrate analyzed by HPLC for 2-methylgluratonitrile, 4-cyanopentanoic acid, and 2-methylglutaric acid. The rate of production of 4-cyanopentanoic acid was 193 mM/h and 198 mM/h, respectively, for uncrosslinked and GA/PEI-crosslinked *Acidovorax facilis* 72W cell/alginate beads. At complete conversion of 2-methylglutaronitrile, the yields of 4-cyanopentanoic acid ammonium salt and 2-methylglutaric acid diammonium salt were typically 98.5% and 1.5% yields, respectively, in either reaction vessel.

At the end of the reaction the product mixtures were decanted from the catalyst beads. These beads were reused in a further eleven consecutive batch reactions under the conditions as described above. As shown in Table 1, the rate of production of 4-cyanopentanoic acid in Reaction 12 was 64 mM/h and 118 mM/h, respectively, for uncrosslinked and GA/PEI-crosslinked *Acidovorax facilis* 72W cell/alginate beads. At the completion of each set of eleven recycle reactions, the final concentration of 4-cyanopentanoic acid was at least 1,550 mM.

TABLE 1

| Reaction # | Uncrosslinked Catalyst Beads (mM 4-CPA/hour) | GA/PEI-Crosslinked Catalyst Beads (mM 4-CPA/hour) |
|---|---|---|
| 1 | 193 | 198 |
| 2 | 137 | 178 |
| 3 | 136 | 173 |
| 4 | 112 | 153 |
| 7 | 86 | 143 |
| 8 | 87 | 143 |
| 9 | 80 | 132 |
| 12 | 64 | 118 |

Example 4

Effect of Calcium Ion Concentration on GA/PEI-Crosslinked *Acidovorax facilis* 72W Cell/Alginate Bead Catalyst for Production of 4-Cyanopentanoic Acid Example 4 illustrates that GA/PEI-crosslinked alginate bead catalyst can be made stable in the presence of high concentrations of ammonium ion. This finding is contrary to the prior art (Klein, J. and Vorlop, K. D., In *Biotechnology Focus I*; Finn, R. F., Ed.; Oxford University Press: New York; 1998, pp 325–336).

Into each of three 125-mL jacketed reaction vessels (temperature-controlled at 30° C. with a recirculating temperature bath) was placed 16.5 g of GA/PEI-crosslinked *Acidovorax facilis* 72W cell/alginate beads prepared as described in Example 2. To each reaction vessel was added 68.25 mL of distilled, deionized water and 14.25 mL (13.54 g, 1.25 M) of 2-methyglutaronitrile. To one of the three reaction mixtures was then added a) 1.0 mL of 0.50 M calcium acetate (pH 7.0), b) 0.20 M calcium acetate (pH 7.0), or c) distilled water, such that the final calcium ion concentrations in the three reaction mixtures were 5.0 mM, 2.0 mM, or 0 mM, respectively. The mixtures were stirred at 30° C. Samples (0.100 mL) of the reaction mixtures were mixed with 0.400 mL of water, and then 0.360 mL of the diluted sample was mixed with 0.040 mL of 0.75 M N-methylpropionamide (HPLC external standard) in water and 0.020 mL of 6.0 N HCl. The resulting mixture was filtered (0.22 µm) and the filtrate analyzed by HPLC for 2-methylgluratonitrile, 4-cyanopentanoic acid and 2-methylglutaric acid. The rates of production of 4-cyanopentanoic acid in reactions containing 5 mM, 2 mM, or 0 mM calcium ion were 236 mM/h, 233 mM/h, and 232 mM/h, respectively.

After complete conversion of 2-methylglutaronitrile, the product mixtures were decanted from the catalyst beads. The catalyst weight was measured and the catalysts were reused in a further ten consecutive batch reactions under the conditions as described above. At complete conversion of 2-methylglutaronitrile in each set of recycle reactions, the final concentration of 4-cyanopentanoic acid was at least 1,550 mM, due to the reaction heel (catalyst plus product mixture) remaining from the previous reaction. The weight of recovered catalyst in each set of reactions is listed in the Table 2.

TABLE 2

| | Catalyst Recovered (grams) | | |
|---|---|---|---|
| Reaction # | 5 mM Calcium Acetate | 2 mM Calcium Acetate | No Calcium Acetate |
| 1 | 16.5 | 16.5 | 16.5 |
| 2 | 15.3 | 15.1 | 15.5 |
| 3 | 15.0 | 14.1 | 14.4 |
| 4 | 14.9 | 13.6 | 14.5 |
| 5 | 14.5 | 13.6 | 14.7 |
| 6 | 14.4 | 13.5 | 12.8 |
| 7 | 14.3 | 13.3 | 10.9 |
| 8 | 14.3 | 13.4 | 8.9 |
| 9 | 14.5 | 13.4 | 7.6 |
| 10 | 14.2 | 13.8 | 7.2 |
| 11 | 14.3 | 13.1 | 6.5 |

The set of three reactions described above was repeated, except that the concentrations of calcium acetate in the three reaction mixtures were 2.0 mM, 1.0 mM, and 0.5 mM, respectively. After a further ten reactions with catalyst recycle, the catalyst beads in reactions containing 0.5 mM calcium acetate broke apart, and the reaction mixture contained a significant quantity of particulate matter. The catalyst beads in reactions containing 1.0 mM calcium acetate began to fracture at twelve reactions with catalyst recycle, and after eighteen reactions the catalyst broke apart and the reaction mixture contained a significant quantity of particulate matter. Catalyst beads in reactions containing 2.0 mM calcium acetate did not break apart, and there was no significant production of particulate matter in the reaction mixtures, after as many as sixty consecutive reactions with catalyst recycle.

Example 5

Immobilization of E. coli Transformant SS1001 Cells in Carrageenan

Example 5 illustrates the immobilization of E. coli transformant SS1001 (ATCC PTA-1177) cells in carrageenan.

Into a 250-mL media bottle (equipped with magnetic stir bar and containing 64.12 g of distilled, deionized water at 50° C.) was slowly added 3.38 g of FMC BioPolymer ISAGEL® RG300 carrageenan with rapid stirring. The mixture was heated to 75–80° C. with rapid stirring until the carrageenan was completely dissolved, and the resulting solution cooled to 55–56° C. (gelling temperature approximately 52° C.) in a thermostated water bath. A suspension (12.5% dry cell weight) of E. coli transformant SS1001 (ATCC PTA-1177) in 0.35 M sodium hydrogen phosphate buffer (45 mL total volume, pH 7.3) was heated to 50° C. for 12 min, then added to the carrageenan solution at 55–56° C. with stirring. The cell/carrageenan mixture was immediately added slowly to 450 mL of soybean oil at 50° C. with stirring using an overhead stirrer. After cell/carrageenan droplets of the desired size were produced in the oil by controlling the stirring rate, the temperature of the oil was reduced to 35° C. to gel the droplets, and the oil decanted from the resulting beads, which were washed with 0.10 M potassium bicarbonate buffer (pH 7.3). A 20-gram portion of the beads was resuspended in 48.8 mL of 0.10 M potassium bicarbonate buffer (pH 7.3), and 0.25 g of 25 wt % glutaraldehyde in water was added and the beads mixed for 1.0 h at 25° C. To the mixture was then added 1.0 g of 12.5 wt % polyethylenimine (BASF Lupasol® PR971L, average molecular weight ca. 750,000) in water, and the beads were mixed for an additional hour at 25° C. The crosslinked beads were then washed with 50 mL of 0.30 M ammonium bicarbonate (pH 7.3) at 25° C. and stored in this same buffer at 5° C.

Example 6

Comparison of Uncrosslinked and GA/PEI-Crosslinked E. coli SS1001/Carrageenan Bead Catalyst for Production of 4-Cyanopentanoic Acid Example 6 illustrates that GA/PEI-crosslinked carrageenan bead catalyst produced 4-cyanopentanoic acid at a higher rate in consecutive batch reactions than uncrosslinked beads.

Into separate 125-mL jacketed reaction vessels (temperature-controlled at 30° C. with a recirculating temperature bath) was placed 12.375 g of either uncrosslinked or GA/PEI-crosslinked E. coli SS1001 (ATCC PTA-1177)/carrageenan beads prepared as described in Example 6. To each reaction vessel was added 51.9 mL of distilled, deionized water containing 20 mM potassium phosphate buffer (pH 7.0) and 10.71 mL (10.17 g, 1.25 M) of 2-methyglutaronitrile, and each mixture was stirred at 30° C. Samples (0.100 mL) of the reaction mixtures were mixed with 0.400 mL of water, then 0.360 mL of the diluted sample was mixed with 0.040 mL of 0.75 M N-methylpropionamide (HPLC external standard) in water and 0.020 mL of 6.0 N HCl. The resulting mixtures were filtered (0.22 μm) and the filtrate analyzed by HPLC for 2-methylgluratonitrile, 4-cyanopentanoic acid, and 2-methylglutaric acid. The rate of production of 4-cyanopentanoic acid was 254 mM/h and 310 mM/h, respectively, for uncrosslinked and GA/PEI-crosslinked of Acidovorax facilis 72W cell/alginate beads. At complete conversion of 2-methylglutaronitrile, the yields of 4-cyanopentanoic acid ammonium salt and 2-methylglutaric acid diammonium salt were 98.8% and 1.2% yields, respectively, in either reaction vessel.

At the end of the reaction the product mixtures were decanted from the catalyst beads. The catalyst beads were reused in a further eleven consecutive batch reactions as described above. Table 3 shows the rate of production of 4-cyanopentanoic acid in Reaction 4 was 120 mM/h and 290 mM/h, respectively, for uncrosslinked and GA/PEI-crosslinked E. coli SS1001 (ATCC PTA-1177)/carrageenan beads.

TABLE 3

| Reaction # | Uncrosslinked Catalyst Beads (mM 4-CPA/hour) | GA/PEI-Crosslinked Catalyst Beads (mM 4-CPA/hour) |
|---|---|---|
| 1 | 254 | 310 |
| 2 | 184 | 290 |
| 3 | 131 | 303 |
| 4 | 120 | 290 |
| 8 | — | 272 |

Example 7

Immobilization of Acidovorax facilis 72W Cells in Carrageenan Example 7 illustrates the immobilization of Acidovorax facilis 72W (ATCC 55746) cells in carrageenan.

Into a 250-mL media bottle (equipped with magnetic stir bar and containing 64.12 g of distilled, deionized water at 50° C.) was slowly added 3.38 g of FMC BioPolymer ISAGEL® RG300 carrageenan with rapid stirring. The mixture was heated to 75–80° C. with rapid stirring until the carrageenan was completely dissolved, and the resulting solution cooled to 55–56° C. (gelling temperature approximately 52° C.) in a thermostated water bath. A suspension of *Acidovorax facilis* 72W cells (12.5% dry cell weight) in 0.35 M sodium hydrogen phosphate buffer (45 mL total volume, pH 7.3) was heated to 50° C. for 60 min, then added to the carrageenan solution at 55–56° C. with stirring. The cell/carrageenan mixture was immediately added slowly to 450 mL of soybean oil at 50° C. with stirring using an overhead stirrer. After cell/carrageenan droplets of the desired size were produced in the oil by controlling the stirring rate, the temperature of the oil was reduced to 35° C. to gel the droplets, and the oil decanted from the resulting beads, which were washed with 0.10 M potassium bicarbonate buffer (pH 7.3). A 20-gram portion of the beads was resuspended in 48.8 mL of 0.10 M potassium bicarbonate buffer (pH 7.3), and 0.25 g of 25 wt % glutaraldehyde in water was added and the beads mixed for 1.0 hour at 25° C. To the mixture was then added 1.0 g of 12.5 wt % polyethylenimine (BASF Lupasol® PR971L, average molecular weight ca. 750,000) in water, and the beads mixed for an additional hour at 25° C. The crosslinked beads were then washed with 50 mL of 0.30 M ammonium bicarbonate (pH 7.3) at 25° C. and stored in this same buffer at 5° C.

Uncrosslinked beads to which no glutaraldehyde had been added were also washed with 0.30 M ammonium bicarbonate (pH 7.3) at 25° C., and stored in this same buffer at 5° C.

Example 8

Comparison of Uncrosslinked and GA/PEI-Crosslinked *Acidovorax facilis* 72W/Carrageenan Bead Catalyst for Production of 4-Cyanopentanoic Acid Example 8 illustrates that GA/PEI-crosslinked carrageenan bead catalyst produced 4-cyanopentanoic acid at a higher rate in consecutive batch reactions than uncrosslinked beads.

Into separate 125-mL jacketed reaction vessels (temperature-controlled at 30° C. with a recirculating temperature bath) was placed 16.5 g of either uncrosslinked or GA/PEI-crosslinked *Acidovorax facilis* 72W/carrageenan beads prepared as described in Example 7. To each reaction vessel was added 72.1 mL of distilled, deionized water containing 50 mM potassium phosphate buffer (pH 7.0) and 11.40 mL (10.83 g, 1.0 M) of 2-methylglutaronitrile, and the mixture stirred at 30° C. Samples (0.100 mL) of the reaction mixture were mixed with 0.400 mL of water, and then 0.360 mL of the diluted sample was mixed with 0.040 mL of 0.75 M N-methylpropionamide (HPLC external standard) in water and 0.020 mL of 6.0 N HCl. The resulting mixture was filtered (0.22 μm) and the filtrate analyzed by HPLC for 2-methylgluratonitrile, 4-cyanopentanoic acid, and 2-methylglutaric acid. The rate of production of 4-cyanopentanoic acid was 266 mM/hour and 235 mM/hour, respectively, for uncrosslinked and GA/PEI-crosslinked *Acidovorax facilis* 72W/alginate beads. At complete conversion of 2-methylglutaronitrile, the yields of 4-cyanopentanoic acid ammonium salt and 2-methylglutaric acid diammonium salt were 98.5% and 1.5% yields, respectively, in either reaction vessel.

At the end of the reaction the product mixtures were decanted from the catalyst beads. The catalyst beads were reused in a further nine consecutive batch reactions as described above. Table 4 shows the rate of production of 4-cyanopentanoic acid in Reaction 9 was 144 mM/hour and 200 mM/hour, respectively, for uncrosslinked and GA/PEI-crosslinked *Acidovorax facilis* 72W/carrageenan beads.

TABLE 4

| Reaction # | Uncrosslinked Catalyst Beads (mM 4-CPA/hour) | GA/PEI-Crosslinked Catalyst Beads (mM 4-CPA/hour) |
| --- | --- | --- |
| 1 | 266 | 235 |
| 2 | 217 | 259 |
| 3 | 193 | 238 |
| 4 | 174 | 235 |
| 7 | 158 | 209 |
| 9 | 144 | 200 |

Example 9

Comparison of *Acidovorax facilis* 72W Cells Immobilized in GA/PEI-crosslinked Alginate or Carrageenan Beads as Catalyst for Production of 4-Cyanopentanoic Acid Example 9 illustrates that the specific activity of nitrilase increases with the increasing concentration of dry cell weight in alginate bead catalyst and not in carrageenan bead catalyst.

Into separate 125-mL jacketed reaction vessels was placed either a) 16.5 g of immobilized *Acidovorax facilis* 72W catalyst beads and 68.25 g distilled, deionized water, or b) 22 g of immobilized *Acidovorax facilis* 72W catalyst beads and 62.75 g distilled, deionized water. The catalyst was chosen from either GA/PEI-crosslinked *Acidovorax facilis* 72W cell/alginate beads (prepared according to the procedure described in Example 2) or GA/PEI-crosslinked *Acidovorax facilis* 72W cell/carrageenan beads (prepared according to the procedure described in Example 5). Catalyst beads were prepared with either 5% dry cell weight (dcw) or 7.5% dew *Acidovorax facilis* 72W cells. For 7.5% dcw catalyst beads, the amount of GA and PEI used to crosslink the beads was increased two-fold to produce completely crosslinked catalyst. To each reaction vessel was immediately added 1.0 mL of 0.20 M calcium acetate buffer (pH 7.0) and 14.25 mL (13.54 g, 1.25 M) of 2-methyglutaronitrile, and each reaction mixture stirred at either 30° C. or 35° C. while maintaining temperature with a recirculating temperature bath. Samples (0.100 mL) of the reaction mixtures were mixed with 0.400 mL of water, then 0.360 mL of the diluted sample was mixed with 0.040 mL of 0.75 M N-methylpropionamide (HPLC external standard) in water and 0.020 mL of 6.0 N HCl. The resulting mixture was filtered (0.22 μm) and the filtrate analyzed by HPLC for 2-methylgluratonitrile, 4-cyanopentanoic acid, and 2-methylglutaric acid. Table 5 lists the reaction rates and catalyst-specific activities for production of 4-cyanopentanoic acid in reactions run with the two catalysts under the same reaction conditions.

TABLE 5

| Temp. (° C.) | Gel Bead | % Gel | % DCW | Grams Catalyst | Rxn Rate (mM/h) | Specific Activity (mmol/h/g) |
|---|---|---|---|---|---|---|
| 30 | alginate | 2.75 | 5.0 | 16.5 | 213 | 1.29 |
| 30 | alginate | 2.75 | 7.5 | 16.5 | 301 | 1.82 |
| 30 | alginate | 2.75 | 7.5 | 22.0 | 377 | 1.71 |
| 35 | alginate | 2.75 | 5.0 | 16.5 | 272 | 1.64 |
| 35 | alginate | 2.75 | 7.5 | 22.0 | 663 | 3.01 |
| 30 | carrageenan | 3.00 | 5.0 | 16.5 | 200 | 1.21 |
| 30 | carrageenan | 3.00 | 7.5 | 16.5 | 213 | 1.29 |
| 35 | carrageenan | 2.25 | 5.0 | 16.5 | 359 | 2.17 |
| 35 | carrageenan | 2.25 | 7.5 | 16.5 | 283 | 1.72 |

Example 10

Preparation of 4-Cyanopentanoic Acid (Ammonium Salt)

Example 10 illustrates that immobilizing *Acidovorax facilis* 72W in alginate removes approximately 90% of unwanted nitrile hydratase activity. In addition, the addition of GA or GA/PEI removes additional unwanted nitrile hydratase activity. Prior art for the preparation of 4-cyanopentanoic acid required a heat-treatment step of the cells to remove the unwanted nitrile hydratase activity (U.S. Pat. No. 5,814,508 and its divisionals supra).

The procedure in Example 2 was repeated to produce three separate *Acidovorax facilis* 72W/alginate bead catalysts, except that the *Acidovorax facilis* 72W (ATCC 55746) cell suspension was not heat-treated at 50° C. for 15 min before mixing with the alginate solution. The nitrilase and nitrile hydratase/amidase activities of the cells were assayed at 25° C. using 0.3 M 2-methylglutaronitrile before immobilization, and the rate of production of 2-methylglutaric acid (2-MGA, a product of the nitrile hydratase/amidase activity of the cells) was 34% of the rate of production of 4-cyanopentanoic acid (4-CPA). For heated cell suspensions prepared as described in Example 2, the rate of production of 2-methylglutaric acid was typically 1.5% of the rate of production of 4-cyanopentanoic acid. For the three sets of catalysts prepared, 1) one set of *Acidovorax facilis* 72W/alginate beads was not crosslinked with either GA or PEI, 2) a second was crosslinked only with GA, and 3) a third was crosslinked with both GA and PEI.

Into three separate 125-mL jacketed reaction vessels (temperature-controlled at 35° C. with a recirculating temperature bath) was placed 16.5 g of one of the three catalysts prepared as described above. To each reaction vessel was then added 68.25 mL of distilled, deionized water, 1.0 mL of 0.20 M calcium acetate buffer (pH 7.0, 2.0 mM final calcium ion concentration in reaction mixture), and 14.25 mL (13.54 g, 1.25 M) of 2-methylglutaronitrile, and the mixture stirred at 35° C. Samples (0.100 mL) of the reaction mixture were mixed with 0.400 mL of water, and then 0.360 mL of the diluted sample was mixed with 0.040 mL of 0.75 M N-methylpropionamide (HPLC external standard) in water and 0.020 mL of 6.0 N HCl. The resulting mixtures were filtered (0.22 $\mu$m) and each filtrate analyzed by HPLC for 2-methylgluratonitrile, 4-cyanopentanoic acid, and 2-methylglutaric acid. The rate of production of 2-methylglutaric acid with *Acidovorax facilis* 72W/alginate beads that were not crosslinked with either GA or PEI was 3.6% of the rate of production of 4-cyanopentanoic acid, a decrease of 34% (Table 6). *Acidovorax facilis* 72W/alginate beads that were crosslinked with only GA had a rate of production of 2-methylglutaric acid that was 1.7% of the rate of production of 4-cyanopentanoic acid, and *Acidovorax facilis* 72W/alginate beads that were crosslinked with both GA and PEI had a rate of production of 2-methylglutaric acid that was 1.5% of the rate of production of 4-cyanopentanoic acid.

TABLE 6

| Catalyst | Cells Heated to 50° C. | GA/PEI Crosslinking | Relative Rate of Production of 2-MGA to 4-CPA (%) |
|---|---|---|---|
| cells | No | no | 34.0 |
| cells | Yes | no | 1.5 |
| cell/alginate beads | No | no | 3.6 |
| cell/alginate beads | No | GA only | 1.7 |
| cell/alginate beads | No | GA and PEI | 1.5 |

Example 11

GA/PEI-Crosslinked *E. Coli* SS1001/Alginate Bead Catalyst For The Production Of 4-Cyanopentanoic Acid The reactions in Example 3 using GA/PEI-crosslinked *Acidovorax facilis* 72W alginate bead catalyst were repeated using GA/PEI-crosslinked *E. coli* SS1001/alginate bead catalyst for the production of 4-cyanopentanoic acid, using 2 mM calcium acetate in the reaction mixture.

After 195 consecutive catalyst recycles, the reaction rate was 67% of the initial reaction rate with no significant loss of the physical integrity of the catalyst beads.

What is claimed is:

1. A method for producing a carboxylic acid comprising:
   a) immobilizing in alginate whole or permeabilized microbial cells having nitrilase activity;
   b) adding, to the immobilized whole or permeabilized microbial cells of step a), a first stabilizer and then a second stabilizer, each in an amount and for a time sufficient to crosslink the immobilized enzyme catalyst, the first stabilizer and the second stabilizer each selected from the group consisting of glutaraldehyde and polyethylenimine, provided the second stabilizer is other than the first stabilizer;
   c) contacting the product of step b) with a nitrile in a suitable aqueous reaction mixture having a $NH_4^+$:$Ca^{2+}$ ratio greater than 20:1 during the course of the reaction;
   d) isolating the carboxylic acid produced in step c) in the form of a salt or an acid; and
   e) optionally repeating steps c) and d).

2. The method of claim 1 wherein the nitrile of step c) is 2-methylglutaronitrile; and the carboxylic acid isolated in step d) is 4-cyanopentanoic acid.

3. The process of claims 1 or 2 wherein the whole or permeabilized microbial cells having nitrilase activity of step (a) are *Acidovorax facilis* 72W (ATCC 55746), *Acidovorax facilis* 72-PF-15 (ATCC 55747), *Acidovorax facilis* 72-PF-17 (ATCC 55745), *Escherichia coli* SS1001 (ATCC PTA-1177), or *Escherichia coli* SW91 (ATCC PTA-1175).

4. The process of claim 3 wherein the enzyme catalyst is *Acidovorax facilis* 72W (ATCC 55746), and wherein a nitrile hydratase activity of the enzyme catalyst is not inactivated by heat before immobilization in alginate.

5. The process of claim 1 or 2 wherein the alginate is calcium alginate.

6. The process of claim 1 or 2 wherein during the course of the reaction the aqueous reaction mixture of step c) has a $NH_4^+:Ca^{2+}$ ratio of at least 200:1 and a calcium ion concentration of at least 2 mM.

7. A method for producing 4-cyanopentanoic acid comprising:
- (a) immobilizing in calcium alginate an enzyme catalyst in the form of whole cells or permeabilized microbial cells selected from the group consisting of *Acidovorax facilis* 72W (ATCC 55746), *Acidovorax facilis* 72-PF-15 (ATCC 55747), *Acidovorax facilis* 72-PF-17 (ATCC 55745), *Escherichia coli* SS1001 (ATCC PTA-1177), and *Escherichia coli* SW91 (ATCC PTA-1175);
- (b) adding, to the immobilized enzyme catalyst of step a), a first stabilizer and then a second stabilizer, each in an amount and for a time sufficient to crosslink the immobilized enzyme catalyst, the first stabilizer and the second stabilizer each selected from the group consisting of glutaraldehyde and polyethylenimine, provided the second stabilizer is other than the first stabilizer;
- (c) contacting the product of step b) with 2-methylglutaronitrile in a suitable aqueous reaction mixture having, during the course of the reaction, a $NH_4^+:Ca^{2+}$ ratio greater than 20:1;
- (d) isolating 4-cyanopentanoic acid produced in step c) in the form of a salt or an acid; and
- (e) optionally repeating steps c) and d).

8. The method of claim 7 wherein the enzyme catalyst is *Acidovorax facilis* 72W (ATCC 55746), and wherein a nitrile hydratase activity of the enzyme catalyst is not inactivated by heat before immobilization in alginate.

* * * * *

UNITED STATES PATENT AND TRADEMARK OFFICE
CERTIFICATE OF CORRECTION

PATENT NO.    : 6,551,804 B2
DATED         : April 22, 2003
INVENTOR(S)   : DiCosimo Robert, Fallon Robert D. and Gavagan John E.

It is certified that error appears in the above-identified patent and that said Letters Patent is hereby corrected as shown below:

<u>Title page, Item [54] and Column 1, lines 1 and 2,</u>
Please change title from "PROCESS FOR PREPARING 4-CYANOPENTANOIC ACID" to read -- IMPROVED PROCESS FOR CONVERTING NITRILES TO CARBOXYLIC ACIDS USING NITRILASE --

Signed and Sealed this

Eighteenth Day of November, 2003

JAMES E. ROGAN
*Director of the United States Patent and Trademark Office*